US008715265B2

(12) United States Patent
Claude et al.

(10) Patent No.: US 8,715,265 B2
(45) Date of Patent: May 6, 2014

(54) DEVICE AND METHOD FOR COMBINING A TREATMENT AGENT AND A GEL

(75) Inventors: Charles D. Claude, San Jose, CA (US); Paul J. Kawula, Sunnyvale, CA (US); Syed Faiyaz Ahmed Hossainy, Fremont, CA (US); Kimchi Tran, Milpitas, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/559,438

(22) Filed: Jul. 26, 2012

(65) Prior Publication Data

US 2012/0289932 A1    Nov. 15, 2012

Related U.S. Application Data

(62) Division of application No. 12/013,286, filed on Jan. 11, 2008, which is a division of application No. 10/187,007, filed on Jun. 28, 2002, now Pat. No. 7,361,368.

(51) Int. Cl.
*A61M 31/00* (2006.01)

(52) U.S. Cl.
USPC ............................ 604/506; 424/426; 604/518

(58) Field of Classification Search
USPC ................. 424/426; 604/82, 85, 506, 518
See application file for complete search history.

(56) References Cited

U.S. PATENT DOCUMENTS

| 2,512,569 | A | 6/1950 | Saffir |
| 3,144,868 | A | 8/1964 | Jascalevich |
| 3,584,624 | A | 6/1971 | de Ciutiis |
| 3,780,733 | A | 12/1973 | Martinez-Manzor |
| 3,804,097 | A | 4/1974 | Rudie |
| 3,890,976 | A | 6/1975 | Bazell et al. |
| 4,141,973 | A | 2/1979 | Balazs |
| 4,617,186 | A | 10/1986 | Schafer et al. |

(Continued)

FOREIGN PATENT DOCUMENTS

| EP | 0331584 | 9/1989 |
| EP | 0861632 | 9/1998 |

(Continued)

OTHER PUBLICATIONS

Abbott Cardiovascular Systems, Non-Final Office Action dated Mar. 13, 2009 for U.S. Appl. No. 10/414,602.

(Continued)

*Primary Examiner* — Nicholas Lucchesi
*Assistant Examiner* — Gerald Landry, II
(74) *Attorney, Agent, or Firm* — Blakely Sokoloff Taylor & Zafman LLP

(57) ABSTRACT

A method including introducing a treatment agent at a treatment site within a mammalian host; and introducing a bioerodable gel material at the treatment site. An apparatus including a first annular member having a first lumen disposed about a length of the first annular member and a first entry port at a proximal end of the first annular member, and a second annular member coupled to the first annular member having a second lumen disposed about a length of the second annular member and a second entry port at a proximal end of the second annular member, wherein the first annular member and the second annular member are positioned to allow a combining of treatment agents introduced through each annular member at the treatment site.

12 Claims, 4 Drawing Sheets

(56) References Cited

U.S. PATENT DOCUMENTS

| | | |
|---|---|---|
| 4,794,931 A | 1/1989 | Yock |
| 4,818,291 A | 4/1989 | Iwatsuki et al. |
| 4,842,590 A | 6/1989 | Tanabe et al. |
| 5,000,185 A | 3/1991 | Yock |
| 5,024,234 A | 6/1991 | Leary et al. |
| 5,026,350 A | 6/1991 | Tanaka et al. |
| 5,049,130 A | 9/1991 | Powell |
| 5,092,848 A | 3/1992 | DeCiutiis |
| 5,100,185 A | 3/1992 | Menke et al. |
| 5,109,859 A | 5/1992 | Jenkins |
| 5,116,317 A | 5/1992 | Carson et al. |
| 5,128,326 A | 7/1992 | Balazs et al. |
| 5,171,217 A | 12/1992 | March et al. |
| 5,202,745 A | 4/1993 | Sorin et al. |
| 5,203,338 A | 4/1993 | Jang |
| 5,242,427 A | 9/1993 | Bilweis |
| 5,270,300 A | 12/1993 | Hunziker |
| 5,291,267 A | 3/1994 | Sorin et al. |
| 5,306,250 A | 4/1994 | March et al. |
| 5,321,501 A | 6/1994 | Swanson et al. |
| 5,328,955 A | 7/1994 | Rhee et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,419,777 A | 5/1995 | Hofling et al. |
| 5,437,632 A | 8/1995 | Engelson |
| 5,455,039 A | 10/1995 | Edelman et al. |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Slepian et al. |
| 5,580,714 A | 12/1996 | Polovina |
| 5,580,856 A | 12/1996 | Prestrelski et al. |
| 5,588,432 A | 12/1996 | Crowley |
| 5,621,610 A | 4/1997 | Moore et al. |
| 5,631,011 A | 5/1997 | Wadstrom |
| 5,642,234 A | 6/1997 | Altman et al. |
| 5,655,548 A | 8/1997 | Nelson et al. |
| 5,667,778 A | 9/1997 | Atala |
| 5,669,883 A | 9/1997 | Scarfone et al. |
| 5,672,153 A | 9/1997 | Lax et al. |
| 5,676,151 A | 10/1997 | Yock |
| 5,693,029 A | 12/1997 | Leonhardt |
| 5,722,403 A | 3/1998 | McGee et al. |
| 5,725,551 A | 3/1998 | Myers et al. |
| 5,730,732 A | 3/1998 | Sardelis et al. |
| 5,740,808 A | 4/1998 | Panescu et al. |
| 5,749,915 A | 5/1998 | Slepian |
| 5,772,665 A * | 6/1998 | Glad et al. ............ 604/82 |
| 5,785,689 A | 7/1998 | De Toledo et al. |
| 5,795,331 A | 8/1998 | Cragg et al. |
| 5,810,885 A * | 9/1998 | Zinger ............ 606/213 |
| 5,811,533 A | 9/1998 | Gold et al. |
| 5,827,313 A | 10/1998 | Ream et al. |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon |
| 5,979,449 A | 11/1999 | Steer |
| 5,980,887 A | 11/1999 | Isner et al. |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,068,599 A * | 5/2000 | Saito et al. ............ 600/454 |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,146,373 A | 11/2000 | Cragg et al. |
| 6,151,525 A | 11/2000 | Soykan |
| 6,152,141 A | 11/2000 | Stevens et al. |
| 6,153,428 A | 11/2000 | Gustafsson et al. |
| 6,159,443 A | 12/2000 | Hallahan et al. |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,192,271 B1 | 2/2001 | Hayman |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | Van Tassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |
| 6,379,379 B1 | 4/2002 | Wang |

(56) References Cited

U.S. PATENT DOCUMENTS

| | | | |
|---|---|---|---|
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,425,887 B1 | 7/2002 | McGuckin et al. |
| 6,432,119 B1 | 8/2002 | Saadat |
| 6,436,135 B1 | 8/2002 | Goldfarb |
| 6,440,947 B1 | 8/2002 | Barron et al. |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,458,098 B1 | 10/2002 | Kanesaka |
| 6,464,862 B2 | 10/2002 | Bennett et al. |
| 6,465,001 B1 | 10/2002 | Hubbell et al. |
| 6,478,775 B1 | 11/2002 | Galt et al. |
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,227 B2 | 4/2003 | Sahatjian et al. |
| 6,544,230 B1 | 4/2003 | Flaherty et al. |
| 6,548,081 B2 | 4/2003 | Sadozai et al. |
| 6,554,801 B1 | 4/2003 | Steward et al. |
| 6,599,267 B1 | 7/2003 | Ray et al. |
| 6,602,241 B2 | 8/2003 | Makower et al. |
| 6,616,869 B2 | 9/2003 | Mathiowitz et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,682,730 B2 | 1/2004 | Mickle et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1* | 3/2004 | Bhat ..................... 604/890.1 |
| 6,726,677 B1 | 4/2004 | Flaherty et al. |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 | 7/2004 | Kavalkovich et al. |
| 6,777,000 B2 | 8/2004 | Ni et al. |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,893,431 B2 | 5/2005 | Naimark et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,270,654 B2 | 9/2007 | Griego et al. |
| 7,273,469 B1 | 9/2007 | Chan et al. |
| 7,361,360 B2 | 4/2008 | Kitabwalla et al. |
| 7,374,774 B2 | 5/2008 | Bowlin et al. |
| 7,393,339 B2 | 7/2008 | Zawacki et al. |
| 7,438,692 B2 | 10/2008 | Tsonton et al. |
| 7,615,373 B2 | 11/2009 | Simpson et al. |
| 7,732,190 B2 | 6/2010 | Michal et al. |
| 7,815,590 B2 | 10/2010 | Cooper |
| 8,187,621 B2 | 5/2012 | Michal |
| 8,192,760 B2 | 6/2012 | Hossainy et al. |
| 2001/0023349 A1 | 9/2001 | Van Tassel et al. |
| 2001/0055615 A1 | 12/2001 | Wallace et al. |
| 2002/0006429 A1* | 1/2002 | Redmond et al. ............ 424/425 |
| 2002/0013408 A1* | 1/2002 | Rhee et al. ................. 525/54.1 |
| 2002/0042473 A1 | 4/2002 | Trollsas et al. |
| 2002/0072706 A1* | 6/2002 | Hiblar et al. ............ 604/101.01 |
| 2002/0076441 A1 | 6/2002 | Shih et al. |
| 2002/0077657 A1* | 6/2002 | Ginn et al. ................. 606/213 |
| 2002/0090725 A1 | 7/2002 | Simpson et al. |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0151867 A1 | 10/2002 | McGuckin et al. |
| 2002/0169420 A1 | 11/2002 | Galt et al. |
| 2002/0188170 A1 | 12/2002 | Santamore et al. |
| 2003/0023202 A1* | 1/2003 | Nielson ......................... 604/80 |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |
| 2003/0125766 A1* | 7/2003 | Ding ............................ 606/213 |
| 2003/0175410 A1 | 9/2003 | Campbell et al. |
| 2003/0233150 A1* | 12/2003 | Bourne et al. ............. 623/23.72 |
| 2004/0002650 A1 | 1/2004 | Mandrusov et al. |
| 2004/0181206 A1 | 9/2004 | Chiu et al. |
| 2004/0185084 A1* | 9/2004 | Rhee et al. ................... 424/426 |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu et al. |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1 | 3/2005 | Lutolf et al. |
| 2005/0070844 A1 | 3/2005 | Chow et al. |
| 2005/0186240 A1 | 8/2005 | Ringeisen et al. |
| 2005/0281883 A1 | 12/2005 | Daniloff et al. |
| 2006/0149392 A1 | 7/2006 | Hsieh et al. |
| 2006/0233850 A1 | 10/2006 | Michal |
| 2007/0270948 A1 | 11/2007 | Wuh |
| 2008/0025943 A1 | 1/2008 | Michal et al. |
| 2009/0022817 A1 | 1/2009 | Michal et al. |
| 2012/0225040 A1 | 9/2012 | Hossainy et al. |
| 2012/0225041 A1 | 9/2012 | Hossainy et al. |

FOREIGN PATENT DOCUMENTS

| | | |
|---|---|---|
| EP | 0938871 | 9/1999 |
| EP | 1214077 | 1/2004 |
| FR | 2715855 | 8/1995 |
| GB | 2194144 | 3/1988 |
| JP | 61205446 | 9/1986 |
| JP | H02145600 | 6/1990 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2001508666 | 7/2001 |
| JP | 2003062089 | 3/2003 |
| JP | 2006014570 | 9/2006 |
| JP | 2007009185 | 1/2007 |
| JP | 2006523507 | 10/2009 |
| WO | WO-9210142 | 6/1992 |
| WO | WO-9315781 | 8/1993 |
| WO | WO-9522316 | 8/1995 |
| WO | WO-9830207 | 7/1998 |
| WO | WO-9854301 | 12/1998 |
| WO | WO-9953943 | 10/1999 |
| WO | WO-0016818 | 3/2000 |
| WO | WO-0054661 | 9/2000 |
| WO | WO-0071196 | 11/2000 |
| WO | WO-0124775 | 4/2001 |
| WO | WO-0124842 | 4/2001 |
| WO | WO-0145548 | 6/2001 |
| WO | WO-0149357 | 7/2001 |
| WO | WO-0200173 | 1/2002 |
| WO | WO-0204008 | 1/2002 |
| WO | WO-0228450 | 4/2002 |
| WO | WO-0240070 | 5/2002 |

(56) References Cited

FOREIGN PATENT DOCUMENTS

| WO | WO-02072166 | 9/2002 |
|---|---|---|
| WO | WO-02087623 | 11/2002 |
| WO | WO-03005961 | 1/2003 |
| WO | WO-03022324 | 3/2003 |
| WO | WO-03022909 | 3/2003 |
| WO | WO-03026492 | 4/2003 |
| WO | WO-03027234 | 4/2003 |
| WO | WO-03064637 | 8/2003 |
| WO | WO-2004000915 | 12/2003 |
| WO | WO-2004050013 | 6/2004 |
| WO | WO 2004058305 | 7/2004 |
| WO | WO-2004060346 | 7/2004 |
| WO | WO-2004066829 | 8/2004 |
| WO | WO 2004091592 | 10/2004 |
| WO | WO-2004098669 | 11/2004 |
| WO | WO-2005061019 | 7/2005 |
| WO | WO-2005067890 | 7/2005 |
| WO | WO 2006027549 | 3/2006 |
| WO | WO-2006039704 | 4/2006 |
| WO | WO-2006014570 | 9/2006 |
| WO | WO 2006113407 | 10/2006 |
| WO | WO-2006113407 | 10/2006 |
| WO | WO-2007048831 | 3/2007 |
| WO | WO-2007145909 | 12/2007 |

OTHER PUBLICATIONS

Abbott Cardiovascular Systems, International search report and written opinion dated Jun. 18, 2009 for PCT/US2008/051505.
Abbott Cardiovascular Systems, Final Office Action mailed Apr. 15, 2011 for U.S. Appl. No. 10/414,602.
Abbott Cardiovascular Systems, Office Action dated Apr. 6, 2009 for U.S. Appl. No. 11/447,340.
Abbott Cardiovascular Systems, Office Action dated Mar. 30, 2009 for U.S. Appl. No. 10/792,960.
Abbott Cardiovascular Systems, Office Action dated Apr. 13, 2009 for U.S. Appl. No. 11/566,643.
Abbott Cardiovascular Systems, Office Action dated May 12, 2009 for U.S. Appl. No. 11/496,824.
Abbott Cardiovascular Systems, Non-Final Office Action dated Mar. 5, 2009 for U.S. Appl. No. 11/507,860.
Abbott Cardiovascular Systems, Non final office action dated Jul. 9, 2009 for U.S. Appl. No. 11/561,328.
Abbott Cardiovascular Systems, Non final office action dated Aug. 5, 2009 for U.S. Appl. No. 11/031,608.
Abbott Cardiovascular Systems, Office Action dated Apr. 29, 2009 for U.S. Appl. No. 12/013,286.
Abbott Cardiovascular Systems, International Preliminary Report on Patentability dated Jul. 30, 2009 for PCT/US2008/051505.
Abbott Cardiovascular Systems, Final office action dated Nov. 12, 2009 for U.S. Appl. No. 12/013,286.
Abbott Cardiovascular Systems, Final office action dated Nov. 25, 2009 for U.S. Appl. No. 11/566,643.
Abbott Cardiovascular Systems, Non final office action dated Dec. 9, 2009 for U.S. Appl. No. 10/781,984.
Abbott Cardiovascular Systems, Examination Report dated Jan. 13, 2010 for EP Application No. 07795729.8.
Abbott Cardiovascular Systems, Non final office action dated Apr. 14, 2010 for U.S. Appl. No. 12/016,180.
Abbott Cardiovascular Systems, Final office action dated Apr. 22, 2010 for U.S. Appl. No. 10/414,602.
Abbott Cardiovascular Systems, Non final office action dated Apr. 29, 2010 for U.S. Appl. No. 10/792,960.
Abbott Cardiovascular Systems, Non-Final Office Action dated Jun. 4, 2010 for U.S. Appl. No. 10/781,984.
Abbott Cardiovascular Systems, Final Office Action dated Jun. 11, 2010 for U.S. Appl. No. 11/561,328.
Abbott Cardiovascular Systems, Final Office Action mailed Jul. 15, 2010, U.S. Appl. No. 11/507,860, 10 pages.
Abbott Cardiovascular Systems, Non final office action dated Aug. 13, 2010 for U.S. Appl. No. 11/447,340.
Abbott Cardiovascular Systems, Final office action mailed Sep. 27, 2010 for U.S. Appl. No. 10/792,960.
Abbott Cardiovascular Systems, Final office action mailed Sep. 27, 2010 for U.S. Appl. No. 12/016,180.
Abbott Cardiovascular Systems, Final Office Action mailed Nov. 22, 2010 for U.S. Appl. No. 10/781,984, 13 pages.
Abbott Cardiovascular Systems, Non-final Office action mailed Nov. 24, 2010 for U.S. Appl. No. 12/013,286, 11 pages.
Abbott Cardiovascular Systems, Non-final Office Action mailed Dec. 8, 2010 for U.S. Appl. No. 11/566,643, 17 pages.
Abbott Cardiovascular Systems, Non-final Office Action mailed Dec. 10, 2010 for U.S. Appl. No. 11/938,752, 32 pages.
Abbott Cardiovascular Systems, Non final office action mailed Feb. 8, 2011 for U.S. Appl. No. 10/792,960.
Abbott Cardiovascular Systems, Non final office action dated Feb. 5, 2010 for U.S. Appl. No. 11/447,340.
Abbott Cardiovascular Systems, Final Office Action dated Jan. 29, 2010 for U.S. Appl. No. 10/792,960.
Abbott Cardiovascular Systems, Examination Report dated Jan. 15, 2010 for EP 08727952.7.
Abbott Cardiovascular Systems, Examination Report dated Feb. 5, 2010 for EP 07810637.4.
Abbott Cardiovascular Systems, Final office action dated Mar. 29, 2010 for U.S. Appl. No. 11/031,608.
Abbott Cardiovascular Systems, Non-final Office Action mailed Dec. 17, 2010 for U.S. Appl. No. 11/933,922, 23 pages.
Abbott Cardiovascular Systems, website for HEALON (R) OVD, copyright 2010, accessed Dec. 15, 2010, URL: <http://abbottmedicaloptics.com/products/cataract/ovds/healon-viscoelastic>, (2010), 2 pages.
Abbott Cardiovascular Systems, Product Information Sheet for HEALON (R), from Abbott Medical Optics, (2005), 1 page.
Abbott Cardiovascular Systems, Japanese Office Action dated Dec. 8, 2010 for Japanese Patent App No. 2006-509975, 6 pages.
Abbott Cardiovascular Systems, Final office action mailed Jul. 18, 2011 for U.S. Appl. No. 11/566,643.
Abbott Cardiovascular Systems, Final office action mailed Sep. 20, 2011 for U.S. Appl. No. 11/938,752.
Abbott Cardiovascular Systems, Final Office Action mailed Oct. 21, 2011 for U.S. Appl. No. 10/781,984, 10 pages.
Abbott Cardiovascular Systems, Final Office Action mailed Jan. 5, 2012 for U.S. Appl. No. 11/361,920, 13 pages.
Abbott Cardiovascular Systems, Non-Final Office Action mailed Jan. 30, 2012 for U.S. Appl. No. 10/781,984, 10 pages.
Abbott Cardiovascular Systems, Final Office Action mailed Feb. 8, 2012 for Japanese application No. 2006-509975, 6 pages.
Abbott Cardiovascular Systems, European Search report for application No. 12151788.2 mailed Apr. 18, 2012, 6 pages.
Abbott Cardiovascular Systems, Non-final Office Action mailed Jun. 22, 2012 for U.S. Appl. No. 12/963,397, 10 pages.
Abbott Cardiovascular Systems, Non final office action mailed Jul. 6, 2011 for U.S. Appl. No. 10/781,984.
Abbott Cardiovascular Systems, Final office action mailed Jun. 28, 2011 for U.S. Appl. No. 10/792,960.
Abbott Cardiovascular Systems, Non-Final Office Action mailed Aug. 31, 2011 for U.S. Appl. No. 11/110,223, 11 pages.
Abbott Cardiovascular Systems, Non final office action mailed Nov. 8, 2011 for U.S. Appl. No. 12/792,960.
Abbott Cardiovascular Systems, Final Office Action mailed Dec. 13, 2011 for U.S. Appl. No. 12/963,397, 15 pages.
Abbott Cardiovascular Systems, Office Action mailed Jan. 17, 2012 for European Patent Application 08727952.7, 6 pages.
Abbott Cardiovascular Systems, Non-Final Office Action mailed Feb. 15, 2012 for U.S. Appl. No. 12/114,717, 16 pages.
Abbott Cardiovascular Systems, Final Office Action mailed Apr. 4, 2012 for U.S. Appl. No. 10/792,960, 13 pages.
Abbott Cardiovascular Systems, European Office Action mailed Apr. 11, 2012 for App No. 12155231.9, 9 pages.
Abbott Cardiovascular Systems, European Office Action mailed Apr. 10, 2012 for App No. 07810637.4, 6 pages.
Abbott Cardiovascular Systems, Final Office Action mailed May 9, 2012 for U.S. Appl. No. 11/110,223, 12 pages.

(56) References Cited

OTHER PUBLICATIONS

Abbott Cardiovascular Systems, Restriction requirement mailed Jul. 3, 2012 for U.S. Appl. No. 13/4722,324, 8 pages.
Abbott Cardiovascular Systems, Non-final Office Action mailed Jun. 26, 2012 for U.S. Appl. No. 12/632,612, 8 pages.
Abbott Cardiovascular Systems, Japanese Office Action dated Jun. 11, 2012 for Appl. No. 2010-162711.
Abbott Cardiovascular Systems, Non final office action mailed Jun. 7, 2011 for U.S. Appl. No. 11/447,340.
Abbott Cardiovascular Systems Inc., PCT Search Report and Written Opinion dated Aug. 26, 2008 for PCT/US2007/016433.
Abbott Cardiovascular Systems Inc., PCT Search Report and Written Opinion dated Jul. 31, 2008 for PCT/US2007/024158.
Abbott Cardiovascular Systems Inc., PCT International Preliminary Report on Patentability and Written Opinion dated Dec. 24, 2008 for PCT/US2007/013181.
Abbott Cardiovascular Systems Inc., "PCT International Search Report and Written Opinion mailed Feb. 10, 2009", PCT/US2007/023419.
Abbott Cardiovascular Systems In, "PCT Search Report dated Feb. 12, 2008", PCT/US2007/013181, 17 pages.
Abbott Cardiovascular Systems Inc., "PCT Search Report dated Jan. 31, 2007", PCT/US2006/014021, 11 pages.
Abbott Cardiovascular Systems Inc., "PCT Search Report dated Mar. 27, 2008", PCT/US2007/003614, 18 pages.
Advanced Cardiovascular Systems, Extended EP Search Report dated May 20, 2011 for EP Application No. 10186197.9.
Advanced Cardiovascular Systems, Extended European search report dated Apr. 21, 2011 for EP Application No. 10186186.2.
Advanced Cardiovascular Systems, Inc., et al., "PCT International Preliminary Report on Patentability dated Jun. 19, 2007", PCT/US2005/045627.
Advanced Cardiovascular Systems, Inc., "PCT International Preliminary Report on Patentability dated Nov. 3, 2005", PCT/US2004/011356, 6 pages.
Advanced Cardiovascular Systems, Inc., "PCT International Search Report and Written Opinion mailed Oct. 13, 2006", PCT/US2005/045627.
Advanced Cardiovascular Systems, Inc., "PCT International Search Report dated Feb. 9, 2004", PCT/US03/30464, 5 pages.
Advanced Cardiovascular Systems, Inc., "PCT International Search Report dated Jan. 28, 2004", PCT/US03/18360, 7 pages.
Advanced Cardiovascular Systems, Inc., "PCT Invitation to Pay Additional Fees mailed Nov. 4, 2003", PCT/US03/18360, 3 pages.
Advanced Cardiovascular Systems, Inc., "PCT Search Report and Written Opinion dated Nov. 24, 2004", PCT/US2004/011356, 12 pages.
Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), (Apr. 1997), pp. 2233-2244.
Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at www.ncbi.nlm.nih.gov/entrez/query.fcgi?cmd=Retrieve&db=PubMed, (Nov. 1997), 229-234.
Anderson, James M., et al., "Biodegradation and biocompatibility of PLA and PLGA microspheres", Advanced Drug Delivery Reviews 28, (1997), 5-24.
Assmus, B., et al., "Transplantation of Progenitor Cells and Regeneration Enhancement in Acute Myocardial Infarction (TOPCARE-AMI),", Clinical Investigation and Reports, Circulation, 106, (2002), 3009-3017.
Baxter Healthcare Corporation, "FloSeal Matrix Hemostatic Sealant", fusionmed.com/docs/surgeon/default.asp, (2002), pp. 1-2.
Berger, et al., "Poly-L-cysteine", J. Am. Chem. Soc., 78(17), (Sep. 5, 1956), pp. 4483-4488.

Bernatowicz, M., et al., "Preparation of Boc-[S-(3-nitro-2-pyridinesulfenyl)]-cysteine and its use for Unsymmetrical Disulfide Bond Formation", Int. J. Peptide Protein Res. 28(2), (Aug. 1996), pp. 107-112.
Boland, E. D., "Electrospinning Collagen and Elastin: Preliminary Vascular Tissue Engineering", Frontiers in Bioscience, vol. 9, (May 1, 2004), pp. 1422-1432.
Brust, G., "Polyimides", Department of Polymer Science; The University of Southern Mississippi, pslc.usm.edu/macrog/imide.htm, (2005), pp. 1-4.
Bull, S., et al., "Self-Assembled Peptide Amphiphile Nanofibers Conjugated to MRI Contrast Agents", Nano Letters, vol. 5, No. 1, (Jan. 2005), 4 pages.
Buschmann, I, et al., "Arteriogenesis versus angiogenesis: Two mechanisms of vessel growth", News Physiol. Sci., vol. 14, (Jun. 1999), 121-125.
Canderm Pharma, "Technical Dossier: Artecoll", downloaded from the Internet on Oct. 22, 2002 from: http://www.canderm.com/artecoll/tech.html, pp. 1-3.
Capan, Y., et al., "Preparation and Characterization of Poly(D,L-lactide-co-glycolide) Microspheres for Controlled Release of Human Growth Hormone", AAPS PharmSciTech., 4(2) Article 28, (2003), 1-10.
Caplan, Michael J., et al., "Dependence on pH of polarized sorting of secreted proteins", Nature, vol. 29, (Oct. 15, 1987), 630.
Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), (Mar. 1990), pp. 1673-1675.
Chandy, et al., "The development of porous alginate/elastin/PEG composite matrix for cardiovascular engineering". Journal of Biomaterials Applications, vol. 17, (Apr. 2003), 287-301.
Choi, Young Seon, et al., "Study on gelatin-containing artificial skin: I. Preparation and characteristics of novel gelatin-alginate sponge", Biomaterials, vol. 20, (1999), 409-417
Chung, Y., et al., "Sol-gel transition temperature of PLGA-g-PEG aqueous solutions", Biomacromolecules, vol. 3, No. 3, (May 2002), 511-516.
Corbett, S., et al., "Covalent Cross-linking of Fibronectin to Fibrin is Required for Maximal Cell Adhesion to a Fibronectin-Fibrin Matrix", The Journal of Biological Chemistry, 272(40), (Oct. 3, 1997), pp. 24999-25005.
Creemers, E., et al., "Matrix Metalloproteinase Inhibition After Myocardial Infarction: A New Approach to Prevent Heart Failure?", Circ. Res., vol. 89, (2001), pp. 201-210.
Crivello, et al., "Synthesis and Photoinitiated Cationic Polymerization of Monomers with the Silsesquioxane Core", J Polym Science: Part A: Polymer Chemistry 35, (1997), pp. 407-425.
Csonka, E., et al., "Interspecific Interaction of Aortic Endothelial and Smooth Muscle Cells", Acta Morphologica Hungarica, vol. 35, No. 1-2, (1987), 31-35.
Davis, M. E., et al., "Injectable Self-Assembling Peptide Nanofibers Create Intramyocardial Microenvironments for Endothelial Cells", Circulation, 111, (Feb. 2005), pp. 442-450.
De Rosa, et al., "Biodegradable Microparticles for the Controlled Delivery of Oligonucleotides", International Journal of Pharmaceutics, 242, (Aug. 21, 2002), pp. 225-228.
Desai, M., et al., "Polymer bound EDC (P-EDC): A convenient reagent for formation of an amide bond", Tetrahedron Letters, 34(48), Abstract downloaded from the Internet at sciencedirect.com, (Nov. 1993), 7685-7688.
Dinbergs, et al., "Cellular response to transforming growth factor-$\beta$1 and basic fibroblast growth factor depends on release kinetics and extracellular matrix interactions", The Journal of Biological Chemistry, vol. 271, No. 47, (Nov. 1996), 29822-29829.
Dong, Zhanfeng, et al., "Alginate/gelatin blend films and their properties for drug controlled release", Journal of Membrane Science, vol. 280, (2006), 37-44.
Edelman, "Controlled and modulated release of basic fibroblast growth factor", Biomaterials, vol. 12, (Sep. 1999), 619-626.
Elbert, D. L. et al., "Protein delivery from materials formed by self-selective conjugate addition reactions", Journal of Controlled Release, 76, (2001), 11-25.

(56) References Cited

OTHER PUBLICATIONS

Etzion, S., et al., "Influence of Embryonic Cardiomyocyte Transplantation on the Progression of Heart Failure in a Rat Model of Extensive Myocardial Infarction", J. Mol. Cell Cardiol., 33, (May 2001), pp. 1321-1330.
Ferrara, N., "Role of Vascular Endothelial Growth Factor in the Regulation of Angiogenesis", Kidney International, 56(3), Abstract downloaded from the Internet at nature.com/ki/journal/v56/n3/abs/4490967a.html, (1999), 794-814.
Friedman, Paul M., et al., "Safety Data of Injectable Nonanimal Stabilized Hyaluronic Acid Gel for Soft Tissue Augmentation", Dermatologic Surgery, vol. 28, (2002), p. 491-494.
Fuchs, S., et al., "Catheter-Based Autologous Bone Marrow Myocardial Injection in No-Option Patients with Advanced Coronary Artery Disease", J. Am. Coll. Cardiol., 41(10), (2003), pp. 1721-1724.
Fukumoto, S., et al., "Protein Kinase C δ Inhibits the Proliferation of Vascular Smooth Muscle Cells by Suppressing G1 Cyclin Expression", The Journal of Biological Chemistry, 272(21), (May 1997), pp. 13816-13822.
Giordano, F., et al., "Angiogenesis: The Role of the Microenvironment in Flipping the Switch", Current Opinion in Genetics and Development, 11, (2001), pp. 35-40.
Gossler, et al., "Transgenesis by means of blastocyst-derived embryonic stem cell lines", Proc. Natl. Acad. Sci. USA, 83, (Dec. 1986), pp. 9065-9069.
Grafe, T. H., "Nanofiber Webs from Electrospinning", Presented at the Nonwovens in Filtration—Fifth International Conference, Stuttgart, Germany, (Mar. 2003), pp. 1-5.
Gref, R., et al., "Biodegradable Long-Circulating Polymeric Nanospheres", Science, 263(5153), Abstract downloaded from the Internet at: http://www.sciencemag.org/cgi/content/abstract/263/5153/1600, 1 page, (Mar. 1994).
Griese, D. P., et al., "Vascular gene delivery of anticoagulants by transplantation of retrovirally-transduced endothelial progenitor cells", Cardiovascular Research, vol. 58, (2003), 469-477.
Grund, F., et al., "Microembolization in Pigs: Effects on Coronary Blood Flow and Myocardial Ischemic Tolerance", Am. J. Physiol., 277 (Heart Circ. Physiol. 46), (1999), pp. H533-H542.
Gupta, et al., "Changes in Passive Mechanical Stiffness of Myocardial Tissue with Aneurysm Formation", Circulation, 89(5), (May 1994), pp. 2315-2326.
Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, (Jan. 1995), 284-288.
Hao, X, et al., "Angiogenic effects of sequential release of VEGF-A165 and PDGF-BB with alginate hydrogels after myocardial infarction", Cardiovascular Research, 75, (2007), 178-185.
Hartgerink, J. D., et al., "Peptide-amphiphile nanofibers: A versatile scaffold for the preparation of self-assembling materials", PNAS, vol. 99, No. 8, (Apr. 16, 2002), 5133-5138.
Hartgerink, J. D., et al., "Self-Assembly and Mineralization of Peptide-Amphiphile Nanofibers", Science, vol. 294, (Nov. 23, 2001), 1684-1688.
Hashimoto, T., et al., "Development of Alginate Wound Dressings Linked with Hybrid Peptides Derived from Laminin and Elastin", Biomaterials, 25, (2004), pp. 1407-1414.
Haugland, et al., "Dialkylcarbocyanine and Dialkylaminostryryl Probes", Handbook of Fluorescent Probes and Research Products, Molecular Probes, Inc., (2002), 530-534.
Haugland, et al., "Membrane-permeant reactive tracers", Handbook of Fluorescent Probes and Research Products, Molecular Probes, Inc., (2002), 458-553.
Haynesworth, Stephen E., et al., "Platelet Effects on Human Mesenchymal Stem Cells", Abstract, presented at Orthopaedic Research Society 48th Annual Meeting, Dallas, TX, (Feb. 10-13, 2010), 2 pages.
Heeschen, C., et al., "Nicotine Stimulates Tumor Angiogenesis", American College of Cardiology, 37(2) Supplement A,, Abstract downloaded from the Internet at: http://24.132.160.238/ciw-01acc/abstract_search_author.cfm?SearchName=Heeschen, 1 page, (Feb. 2001), pp. 1A-648A.
Helisch, A, et al., "Angiogenesis and arteriogenesis", NEUE Diagnostische Und Therap. Verfahren, Z Kardiol 89, (2000), 239-244.
Hendel, R. C., et al., "Effect of Intracoronary Recombinant Human Vascular Endothelial Growth Factor on Myocardial Perfusion: Evidence for a Dose-Dependent Effect", Circulation, 101, (2000), pp. 118-121.
Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at www.diabetes.diabetesjournals.org/cgi/content/abstract/44/8/936, (1995), pp. 936-946.
Hoffman, "Hydrogels for Biomedical Applications", Advanced Drug Delivery Reviews, vol. 43, (2002), pp. 3-12.
Holland, N. B., et al., "Biomimetic Engineering of Non-Adhesive glycocalyx-like Surfaces Using Oligosaccharide Surfactant Polymers", Nature, 392, Abstract downloaded from the Internet at www.nature.com, (Apr. 1998), pp. 799-801.
Horan, R.L., et al., "In Vitro Degradation of Silk Fibroin", Biomaterials, vol. 26, (2004), 3385-3393.
Hovinen, J., et al., "Synthesis of 3'-functionalized oligonucleotides on a single solid support", Tetrahedron Letters, 34(50), Abstract downloaded from the Internet at www.sciencedirect.com, (Dec. 1993), pp. 8169-8172.
Huang, K., et al., "Synthesis and Characterization of Self-Assembling Block Copolymers Containing Bioadhesive End Groups", Biomacromolecules, 3(2), (2002), pp. 397-406.
Hutcheson, K., et al., "Comparison of Benefits on Myocardial Performance of Cellular Cardiomyoplasty with Skeletal Myoblasts and Fibroblasts", Cell Transplantation, 9(3), (2000), pp. 359-368.
Huynh, T. V., et al., "Constructing and Screening cDNA Libraries in λgt10 and λgt11", Chapter 2 in DNA Cloning, Volume 1: A Practical Approach, ed. by D.M. Glover, (1985), pp. 49-78.
Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, (Jul. 1990) pp. 80-86
Iskandrian, A. S., et al., "Nuclear Cardiac Imaging: Principles and Applications", second edition, F.A. Davis Co., Philadelphia, cover page, title page and TOC, (1996), 5 pages total.
Isner, J. M. "Vascular Endothelial Growth Factor: Gene Therapy and Therapeutic Angiogenesis", Am. J. Cardiol., 82(10A), (Nov. 19, 1998), pp. 63S-64S.
Ito, Wulf D., et al., "Monocyte chemotactic protein-1 increases collateral and peripheral conductance after femoral artery occlusion", Max-Planck-Institute for Physiology and Clinical Research, Bad Nauheim, Germany, (Feb. 21, 1997), 829-837.
Johnson, et al., "The stabilization and encapsulation of human growth hormone nto biodegradable microspheres", Pharmaceutical Research, vol. 14, No. 6, (1997), 730-735.
Jonasson, P., et al., "Denatured states of human carbonic anhydrase II: an NMR study of hydrogen/deuterium exchange at tryptophan-indole-Hn sites", FEBS Letters, 445, (1999), p. 361-365.
Kalltorp, Mia, et al., "Inflammatory cell recruitment, distribution, and chemiluminescence response at IgG precoated- and thiol functionalized gold surfaces", Swedish Biomaterials Consortium, Swedish Foundation for Strategic Research, (Apr. 9, 1999), 251-259.
Kaplan, D.L., et al., "Spiderless Spider Webs", Nature Biotechnology, vol. 20, (2002), 239-240.
Kawai, et al., "Accelerated tissue regeneration through incorporation of basic fibroblast growth factor-impregnated gelatin microspheres into artificial dermis", Biomaterials, 21(5), (Mar. 2000), 489-499.
Kawasuji, M., et al., "Therapeutic Angiogenesis with Intramyocardial Administration of Basic Fibroblast Growth Factor", Ann Thorac Surg, 69, Abstract downloaded from the Internet at www.ats.ctsnetjournals.org/cgi/content/abstract/69/4/1155, (2000), pp. 1155-1161.

(56) References Cited

OTHER PUBLICATIONS

Kelley, et al., "Restraining Infarct Expansion Preserves Left Ventricular Geometry and Function After Acute Anteroapical Infarction", Circulation, 99, (1999), pp. 135-142.

Kelly, E. B., "Advances in Mammalian and Stem Cell Cloning", Genetic Engineering News, vol. 23, No. 7, (Apr. 1, 2003), pp. 17-18 & 68.

Khademhosseini, et al., "Microscale Technologies for Tissue Engineering and Biology", PNAS, vol. 103, No. 8, (Feb. 21, 2006), pp. 2480-2487.

Kim, D., et al., "Glow Discharge Plasma Deposition (GDPD) Technique for the Local Controlled Delivery of Hirudin from Biomaterials", Pharmaceutical Research, 15(5), (1998), 783-786.

Kim, Ung-Jin, et al., "Structure and Properties of Silk Hydrogels", Biomacromolecules, vol. 5(3), (2004), 786-792.

Kinart, et al., "Electrochemical Studies of 2-hydroxy-3-(3,4-dimethyl-9-oxo-9H-thioxanthen-2-yloxy)N,N,N-trimethyl-1-propanium chloride", J. Electroanal. Chem, 294, (1990), pp. 293-297.

Kipshidze, Nicholas, et al., "Therapeutic angiogenesis for critical limb ischemia to limit or avoid amputation", University of Wisconsin Medical School, The Journal of Invasive Cardiology, vol. 11, No. 1, (Jan. 1999), 25-28.

Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, (1997) pp. 159-192.

Klugherz, Bruce D., et al., "Gene delivery from a DNA controlled-release stent in porcine coronary arteries", Nature Biotechnology, vol. 18, (Nov. 2000), 1181-1184.

Kohilas, K, et al., "Effect of prosthetic titanium wear debris on mitogen-induced monocyte and lymphoid activation", John Hopkins University, Dept. of Orthopaedic Surgery, (Apr. 1999), 95-103.

Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, (Jan. 2001), 1848-1853.

Kwok, C., et al., "Design of Infection-Resistant Antibiotic-Releasing Polymers: I. Fabrication and Formulation", Journal of Controlled Release, 62, (1999), pp. 289-299.

Laboratory of Liposome Research, "Liposomes: General Properties", downloaded from the Internet on Feb. 9, 2006 at www.unizh.ch/onkwww/lipos.htm.

Laham, R. J., "Intrapericardial Delivery of Fibroblast Growth Factor-2 Induces Neovascularization in a Porcine Model of Chronic Myocardial lschemia", J. Pharmacol Exper Therap, 292(2), (2000), pp. 795-802.

Leibovich, S. J., et al., "Macrophage-Induced Angiogenesis is Mediated by Tumour Necrosis Factor-α", Nature, vol. 329, (Oct. 15, 1987), pp. 630-632.

Leor, J., et al., "Bioengineered Cardiac Grafts—A New Approach to Repair the Infarcted Myocardium?", Circulation, 102[suppl III], (2000), pp. III-56-III-61.

Leor, J., et al., "Gene Transfer and Cell Transplant: An Experimental Approach to Repair a 'Broken Heart'", Cardiovascular Research, 35, (1997), pp. 431-441.

Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at www.ncbi.nlm.nih.gov/entrez/query.fcgi?cmd=Retrieve&db=pubmed, (1995), pp. 695-703.

Lewin, B., "Repressor is Controlled by a Small Molecule Inducer", Genes VII, Oxford University Press, 7th ed., (2000), pp. 277-280.

Li, et al., "Cell Therapy to Repair Broken Hearts", Can. J. Cardiol., vol. 14, No. 5, (May 1998), pp. 735-744.

Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, (2000), Chapter 33.

Li, J., et al., "PR39, A Peptide Regulator of Angiogenesis", Nature Medicine, 6(1), (Jan. 2000), pp. 49-55.

Li, B., et al., "VEGF and PIGF promote adult vasculogenesis by enhancing EPC recruitment and vessel formation at the site of tumor neovascularization", The FASEB Journal, vol. 20, (2006), 1495-1497.

Li., Y. Y., et al., "Differential Expression of Tissue Inhibitors of Metalloproteinases in the Failing Human Heart", Circulation, 98(17), (1998), pp. 1728-1734.

Lindsey, M., et al., "Selective Matrix Metalloproteinase Inhibition Reduces Left Ventricular Remodeling but does not Inhibit Angiogenesis after Myocardial Infarction", Circulation, 105(6), (2002), pp. 753-758.

Long, D. M., et al., "Self-Cleaving Catalytic RNA", FASEB Journal, 7, (1993), pp. 25-30.

Lopez, J. J., et al., "Angiogenic potential of perivascular delivered aFGF in a porcine model of chronic myocardial ischemia", The American Physiological Society, 0363-6135/98, (1998), H930-H936.

Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, (1998), pp. 272-281.

Lu, L., et al., "Biodegradable Polymer Scaffolds for Cartilage Tissue Engineering", Clinical Orthopaedics and Related Research, Carl T. Brighton (ed.). No. 391S, (2001), pp. S251-270.

Luo, Y., et al., "Cross-linked Hyaluronic Acid Hydrogel Films: New Biomaterials for Drug Delivery", Journal of Controlled Release, 69, (2000), pp. 169-184.

Lutolf, M, et al., "Synthesis and Physicochemical Characterization of End-Linked Poly(ethylene glycol)-co-peptide Hydrogels Formed by Michael-Type Addition", Biomacromolecules, vol. 4, (2003), 713-722.

Lyman, M. D., et al., "Characterization of the Formation of Interfacially Photopolymerized Thin Hydrogels in Contact with Arterial Tissue", Biomaterials, 17(3), (1996), pp. 359-364.

Mansour, S., et al., "Disruption of the proto-oncogene int-2 in mouse embryo-derived stem cells: a general strategy for targeting mutations to non-selectable genes", Nature, 336, (1988), pp. 348-352.

Martin, S. L., et al., "Total Synthesis and Expression in *Escherichia Coli* of a Gene Encoding Human Tropoelastin", Gene, (1995), Abstract.

McDevitt, T., et al., "In vitro Generation of Differentiated Cardiac Myofibers on Micropatterned Laminin Surfaces", J. Biomed Mater Res., 60, (2002), pp. 472-479.

Meinel, L., et al., "The Inflammatory Responses to Silk Films In Vitro and In Vivo", Biomaterials, vol. 26, (2005), 147-155.

Narmoneva, D. A., et al., "Self-assembling short oligopeptides and the promotion of angiogenesis", Biomaterials, 26, (2005), pp. 4837-4846.

Nazarov, R., et al., "Porous 3-D Scaffolds from Regenerated Silk Fibroin", Biomacromolecules, vol. 5(3), (2004), 718-726.

Nguyen, K. T., et al., "Photopolymerizable Hydrogels for Tissue Engineering Applications", Biomaterials, 23, (2002), pp. 4307-4314.

Nikolic, S. D., et al., "New Angiogenic Implant Therapy Improves Function of the Ischemic Left Ventricle", Supplement to Circulation; Abstracts From Scientific Sessions 2000, 102(18), (Oct. 2000), pp. II-689, Abstract 3331.

Nikolic, Serjan D., et al., "Novel means to improve coronary blood flow", Clinical Science, Abstracts from Scientific Sessions, (2000), II-689.

Nitinol Technical Information, "NiTi Smart Sheets", downloaded from the Internet on Dec. 10, 2002 at: http://www.sma-inc.com/information.html, 1 page.

Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, (Dec. 1986), 2649-2658.

Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), (1977), pp. 90-92.

(56) References Cited

OTHER PUBLICATIONS

Ozbas, B., et al., "Salt-Triggered Peptide Folding and Consequent Self-Assembly into Hydrogels with Tunable Modulus", Macromolecules, 37(19), (2004), pp. 7331-7337.

Ozbas-Turan, S., "Controlled Release of Interleukin-2 from Chitosan Microspheres", Journal of Pharmaceutical Sciences, 91(5), (May 2002), pp. 1245-1251.

Palmiter, R., et al., "Germ-Line Transformation of Mice", Ann. Rev. Genet., 20, (1986), pp. 465-499.

Patrick, C. R., "Mixing and Solution Properties of Organofluorine Compounds", Preparation, Properties and Industrial Applications of Organofluorine Compounds, Chapter 10, R.E. Banks (ed,), 1st edition, Ellis-Horwood Ltd., Chichester:England, (1982), pp. 323-342.

Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, (Jun. 2004).

Penta, K., et "Del1 Induces Integrin Signaling and Angiogenesis by Ligation of αVβ3", J. Biolog. Chem., 274(16), (Apr. 1999), pp. 11101-11109.

Perin, E. C., et al., "Transendocardial, Autologous Bone Marrow Cell Transplantation for Severe, Chronic, Ischemic Heart Failure", Circulation, (2003).

Pouzet, B., et al., "Is Skeletal Myoblast Transplantation Clinically Relevant in the Era of Angiotensin-Converting Enzyme Inhibitors?", Circulation, 104 [suppl I], (Sep. 2001), pp. I-223-I-228.

Prather, et al., "Nuclear Transplantation in Early Pig Embryos", Biol. Reprod., 41, (1989) pp. 414-418.

Prosci Incorporated, "ILPIP (CT) Peptide".

Quellec, P., et al., "Protein Encapsulation Within Polyethylene Glycol-coated Nanospheres. I. Physicochemical Characterization", J. Biomed. Mater. Res., 42(1), (1998)), Abstract.

Ramirez-Solis, R., et al., "Gene Targeting in Embryonic Stem ", Methods in Enzymology, 225, (1993) pp. 855-878.

Ritter, A. B., et al., "Elastic modulus, distensibility, and compliance (capacitance)", Biomedical Engineering Principles, Chapter 4, (2005), 187-191.

Rowley, et al., "Alginate Hydrogels as Synthetic Extracelllular Matrix Materials", Biomaterials, 20(1), (1999), 45-53.

Sawhney, A. S., et al., "Bioerodible Hydrogels Based on Photopolymerized Poly(ethylene glycol)-co-poly(a-hydroxy acid) Diacrylate Macromers", Macromolecules, 26(4), (1993), pp. 581-587.

Sbaa-Ketata, E., et al., "Hyaluronan-Derived Oligosaccharides Enhance SDF-1-Dependent Chemotactic Effect on Peripheral Blood Hematopoietic CD34+ Cells", Stem Cells, 20(6), Letter to the Editor downloaded from the Internet at www.stemcells.alphamedpress.org/cgi/content/full/20/6/585, (2002), 585-587.

Seeger, J. M., et al., "Improved in vivo endothelialization of prosthetic grafts by surface modification with fibronectin", J Vasc Surg, vol. 8, No. 4, (Oct. 1988), 476-82 (Abstract ony).

Segura, T, et al., "Crosslinked Hyaluronic Acid Hydrogels: A Strategy to Functionalize and Pattern", Biomaterials, vol. 26(4), (Feb. 2005), 359-371.

Segura, T, et al., "DNA delivery from hyaluronic acid-collagen hydrogels via a substrate-mediated approach", Biomaterials, vol. 26, (2005), 1575-1584.

Segura, T., et al., "Substrate-Mediated DNA Delivery: Role of the Cationic Polymer Structure and Extent of Modification", Journal of Controlled Release, 93, (2003), pp. 69-84.

Segura, T., et al., "Surface-Tethered DNA Complexes for Enhanced Gene Delivery", Bioconjugate Chem, 13(3), (2002), pp. 621-629.

Shibasaki, F., et al., "Suppression of Signalling Through Transcription Factor NF-AT by Interactions Between Calcineurin and Bcl-2", Nature, 386(6626), Abstract downloaded from the Internet at www.ncbi.nlm.nih.gov/entrez/query.fcgi?CMD=Text&DB=pubmed, (1997).

Shin, H., et al., "Attachment, Proliferation, and Migration of Marrow Stromal Osteoblasts Cultured on Biomimetic Hydrogels Modified with an Osteopontin-Derived Peptide", Biomaterials, 25, (2004), pp. 895-906.

Shin, H., et al., "In vivo bone and soft tissue response to injectable, biodegradable oligo(poly(ethylene glycol) fumarate) hydrogels", Biomaterials 24, Elseview Science Ltd., (3201-3211), 2003.

Shu, Z, et al., "Disulfide-crosslinked hyaluronan-gelatin hydrogel films: a covalent mimic of the extracellular matrix for in vitro cell growth", Biomaterials, vol. 24(21), (Sep. 2003), 3825-3834.

Shu, Zheng, et al., "In situ crosslinkable hyaluronan hydrogels for tissue engineering", Biomaterials, vol. 25, No. 7-8, (Mar. 2004), 1339-1348.

Simons, M., et al., "Clinical trials in coronary angiogenesis: Issues, problems, consensus, An expert panel summary", Angiogenesis Research Center, American Heart Association, Inc.,, (Sep. 12, 2000), 1-14.

Spenlehauer, G, et al., "In vitro and in vivo degradation of poly(D,L lactide/glycolide) type microspheres made by solvent evaporation method", Biomaterials, vol. 10, (Oct. 1989), 557-563.

Spinale, F. G., "Matrix Metalloproteinases—Regulation and Dysregulation in the Failing Heart", Circ. Res., 90, (2002), pp. 520-530.

Springer, M., et al., "Angiogenesis Monitored by Perfusion with a Space-Filling Microbead Suspension", Mol. Ther., 1(1), Abstract downloaded from the Internet at www.ncbi.nlm.nih.gov/entrez/query.fcgi?cmd=Retrieve&db=PubMed, (2000), pp. 82-87.

Staatz, WD, et al., "Identification of a tetrapeptide recognition sequence for the alpha 2 beta 1 integrin in collagen", Journal of Biological Chemistry, 1991, 266(12), pp. 7363-7367.

Storm, G., et al., "Surface Modification of Nanoparticles to Oppose Uptake by the Mononuclear Phagocyte System", Advanced Drug Delivery Reviews, 17(1), Abstract downloaded from the Internet at www.sciencedirect.com, (Oct. 1995), pp. 31-48.

Strauer, B., et al., "Repair of Infarcted Myocardium by Autologous Intracoronary Mononuclear Bone Marrow Cell Transplantation in Humans", Circulation, 106, (2002), pp. 1913-1918.

Tybulewicz, V., et al., "Neonatal lethality and lymphopenia in mice with a homozygous disruption of the c-abl proto-oncogene", Cell, 65(7), Abstract downloaded from the Internet at www.sciencedirect.com, (Jun. 1991) pp. 1153-1163.

Unger, E. F., et al., "Effects of a Single Intracoronary Injection of Basic Fibroblast Growth Factor in Stable angina Pectoris", Am. J. Cardiol, 85(12), Abstract downloaded from the Internet at www.sciencedirect.com, (Jun. 2000), pp. 1414-1419.

Urbich, C., et al., "Endothelial Progenitor Cells: Characterization and Role in Vascular Biology", Circulation Research, vol. 95, (2004), 343-353.

Van Der Giessen, Willem J., et al., "Marked inflammatory sequelae to implantation of biodegradable and nonbiodegradable polymers in porcine coronary arteries", Dept. of Cardiology, Erasmus University Rotterdam, Circulation, vol. 94, No. 7, (Oct. 1, 1996), 1690-1697.

Van Luyn, M. J., et al., "Cardiac Tissue Engineering: Characteristics of In Unison Contracting Two- and Three-Dimensional Neonatal Rat Ventricle Cell (Co)-Cultures", Biomaterials, 23, (2002), pp. 4793-4801.

Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at pubs.acs.org/cgi-bin/abstract.cgi/bcches/1997/8/i05/abs/bc9701095.html, (1997), pp. 686-694.

Visscher, G.E., et al., "Tissue response to biodegradable injectable microcapsules", Journal of Biomaterials Applications, vol. 2, (Jul. 1987), 118-119.

Vlodavsky, I., et al., "Extracellular Matrix-resident Basic Fibroblast Growth Factor: Implication for the Control of Angiogenesis", J. Cell Biochem, 45(2), Abstract downloaded from the Internet at www.ncbi.nlm.nih.gov/entrez/query.fcgi?cmd=Retrieve&db=PubMed, (Feb. 1991), pp. 167-176.

Wang, M., et al., "Mechanical Properties of Electrospun Silk Fibers", Macromolecules, vol. 37(18), (2004), 6856-6864.

(56) References Cited

OTHER PUBLICATIONS

Wilensky, R., et al., "Direct intraarterial wall injection of microparticles via a catheter: a potential drug delivery strategy following angioplasty", American Heart Journal, 122, (1991), p. 1136.
Witzenbichler, B., et al., "Vascular Endothelial Growth Factor-C (VEGF-C/VEGF-2) Promotes Angiogenesis in the Setting of Tissue Ischemia", AM Pathol., 153(2), (Aug. 1998), pp. 381-394.
Yager, P., et al., "Silk Protein Project", www.faculty.washington.edu/yagerp/silkprojecthome.html, (Aug. 23, 1997), pp. 1-16.
Yeo, L.Y., et al., "AC Electrospray Biomaterials Synthesis", Biomaterials, (2005), 7 pages.
Zervas, L., et al., "On Cysteine and Cystine Peptides. II. S-Acylcysteines in Peptide Synthesis", J. Am. Chem. Soc., 85(9), (May 1963), pp. 1337-1341.
Zheng, Shu, et al., "In situ crosslinkable hyaluronan hydrogels for tissue engineering", Biomaterials, Elsevier Science Publishers, vol. 25, No. 7-8, (2004), 1339-1348.
Zheng, W., "Mechanisms of coronary angiogenesis in response to stretch; role of VEGF and TGF-Beta", AM J Physiol Heart Circ Physiol 280(2), (Feb. 2001), H909-H917.
Zimmermann, W., et al., "Engineered Heart Tissue for Regeneration of Diseased Hearts", Biomaterials, 25, (2004), pp. 1639-1647.
Abbott Cardiovascular Systems, et al., Japanese Office Action dated Nov. 19, 2012 for JP Appln. No. 2009-539265.
Abbott Cardiovascular Systems, et al., Final Office Action mailed Nov. 7, 2012 for U.S. Appl. 10/781,984.
Abbott Cardiovascular Systems, et al., Final Office Action dated Nov. 8, 2012 for U.S. Appl. 12/114,717.
Abbott Cardiovascular Systems, et al., Japanese Office Action dated Aug. 27, 2012 for JP 2009-522776.
Abbott Cardiovascular Systems, et al., Final office action mailed Nov. 7, 2012 for U.S. Appl. No. 10/781,984.
Abbott Cardiovascular Systems, et al., Non-Final Office Action dated Oct. 3, 2012 for U.S. Appl. No. 12/756,119.
Abbott Cardiovascular Systems, et al., Non-final Office Action mailed Aug. 30, 2012 for U.S. Appl. No. 13/472,328.
Abbott Cardiovascular Systems, et al., Non-final Office Action mailed Aug. 28, 2012 for U.S. Appl. No. 13/472,324.
Abbott Cardiovascular Systems, et al., Japanese office action dated Aug. 20, 2012 for JP Appl. No. 2009-537153.
Abbott Cardiovascular Systems, et al., Non-Final Office Action dated Sep. 11, 2012 for U.S. Appl. No. 10/792,960.
Davis, M. E., et al., "Injectable Self-Assembling Peptide Nanofibers Create Intramyocardial Microenvironments for Endothelial Cells", Circulation, 111, (2005), 442-450.
Hao, X, et al., "Angiogenic Effects of Sequential release of VEGF-A 165 and PDGF-BB with Alginate Hydrogels After Myocardial Infarction", Cardiovascular Research, 75(1), (Apr. 6, 2007), 178-185.
Mogan, L., "Rationale of platelet gel to augment adaptive remodeling of the injured heart", J Extra Corpor Technol, 36(2), (Jun. 2004), 191-196.
Wasielewski, "Ischamische Erkrankungen, Gefassneubildung anregen", Deutsche Apotheker Zeitung, vol. 140, No. 3, Stuttgart (DE), (Jan. 20, 2000), 232-233.
Yamamoto, N. , et al., "Histologic evidence that basic fibroblast growth factor enhances the angiogenic effects of transmyocardial laser revascularization", Basic Research in Cardiology, vol. 95, No. 1, (Feb. 1, 2000), 55-63.
Abbott Cardiovascular Systems, Final office action dated Jan. 18, 2013 for U.S. Appl. No. 12/963,397.
Abbott Cardiovascular Systems, Japanese office action dated Oct. 9, 2012 for JP Appln. No. 2009-514330.
Abbott Cardiovascular Systems, Examination Report dated Feb. 20, 2013 for European Appln. No. 12151788.2, 4 pages.
Abbott Cardiovascular Systems, Non final office action dated Apr. 1, 2013 for U.S. Appl. No. 13/559,423.
Abbott Cardiovascular Systems, Non-Final Office Action dated Oct. 3, 2012 for U.S. Appl. No. 12/756,092.
Abbott Cardiovascular Systems, Final office action mailed Apr. 22, 2013 for U.S. Appl. No. 10/792,960.
Abbott Cardiovascular Systems, Japanese office action mailed Mar. 25, 2013 for JP 2009-539265.
Abbott Cardiovascular Systems, Japanese Office Action mailed Dec. 17, 2012 for JP Appln. No. 2009-546553.
Abbott Cardiovascular Systems, Non final office action mailed Jul. 2, 2013 for U.S. Appl. No. 11/938,752.
Abbott Cardiovascular Systems, Non final office action dated Aug. 20, 2013 for U.S. Appl. No. 12/114,717.
Abbott Cardiovascular Systems, Non-Final Office Action mailed Oct. 16, 2013 for U.S. Appl. No. 13/468,956.

\* cited by examiner

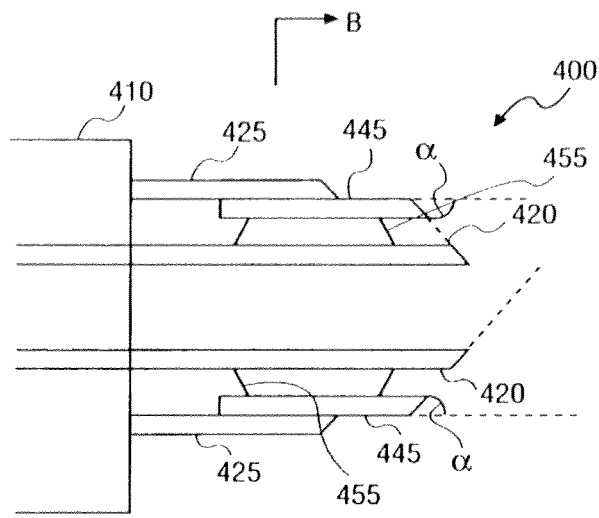
FIG. 5
FIG. 6
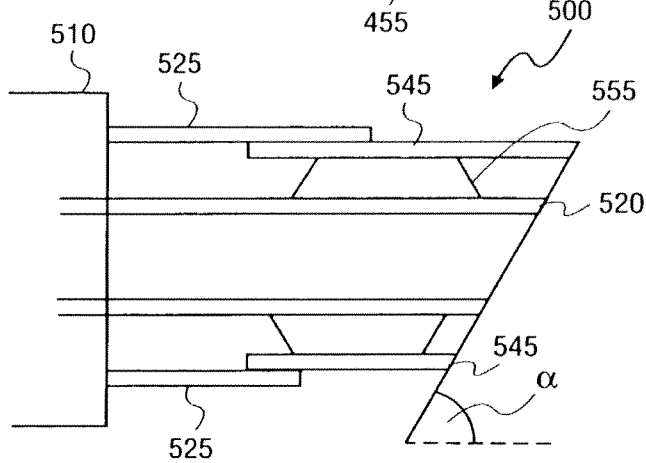
FIG. 7

DEVICE AND METHOD FOR COMBINING A TREATMENT AGENT AND A GEL

CROSS-REFERENCE TO RELATED APPLICATION

The application is a divisional of U.S. patent application Ser. No. 12/013,286, filed Jan. 11, 2008, which is a divisional of U.S. patent application Ser. No. 10/187,007, filed Jun. 28, 2002 (now U.S. Pat. No. 7,361,368), and incorporated herein by reference.

BACKGROUND

1. Field

The invention relates to retaining a treatment agent at a treatment site with a bioerodable gel.

2. Relevant Art

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by natural processes, in which new vessels are formed (termed "angiogenesis") and small vessels are enlarged (termed "arteriogenesis") to replace the function of the impaired vessels. These new conduits may facilitate restoration of blood flow to the deprived tissue, thereby constituting "natural bypasses" around the occluded vessels. However, some individuals are unable to generate sufficient collateral vessels to adequately compensate for the diminished blood flow caused by cardiovascular disease. Accordingly, it would be desirable to provide a method and apparatus for delivering agents to help stimulate the natural process of therapeutic angiogenesis to compensate for blood loss due to an occlusion in a coronary and peripheral arteries in order to treat ischemia.

In some therapies, e.g., cardiovascular-related, cancer-related, and certain surgical or minimally-invasive therapies, it may be desirable to inject a treatment agent of or including a sustained release matrix intralumenally, intracardially, or intraventricularly. Unfortunately, however, it is generally difficult to retain the treatment agent at a desired treatment site. In cardiovascular-related therapies, for example, rarely is greater than 30 percent of the sustained release matrix retained at the injection site following such therapies. The loss of sustained release matrix generally occurs either during the initial injection or as a result of backflow from the needle site. The backflow from the needle site can occur due to an excessive amount of fluid required to deliver the matrix material, or, as the needle is removed from the injection site, the site does not seal before matrix material escapes. The consequences of matrix material escaping can be multifold depending on the interaction of the matrix and the surrounding blood or fluid.

The loss of matrix material and release can result in inconsistent dosage delivery. The inconsistency in dosage delivery in turn results in the delivery of the treatment agent that possibly will be at a dosage outside of the desired or optimum therapeutic window. In the case of arterial or ventricular treatment sites, a second response would occur if the sustained release matrix has thrombogenic effects, resulting in the formation of thrombosis that may have severe consequences in the arterial or ventricular region.

What is needed is a technique for retaining a treatment agent, including a treatment agent of or including a sustained-release matrix at a treatment site.

SUMMARY

A method is disclosed. In one embodiment, the method includes introducing a treatment agent at a treatment site within a mammalian host and introducing a bioerodable gel at the treatment site. Representatively, the gel includes a substance that will retain the treatment agent at a desired treatment site. In one example, the treatment agent and gel may be introduced as a combination. Alternatively, the treatment agent and gel may be introduced sequentially, such as introducing the gel before and/or after the treatment agent. The gel may serve, in one aspect, to retain the treatment agent at the treatment site for a prolonged period of time so as to beneficially stimulate the effect of a treatment agent. Suitable treatment sites representatively include, but are not limited to, in or around a blood vessel such as a coronary blood vessel, thoroscopic surgery sites, orthoscopic surgery sites, and laparoscopic surgery sites.

In another embodiment, a method includes introducing a delivery device at a location in a blood vessel and advancing the delivery device a distance into a wall (including entirely through the wall) of the blood vessel to a treatment site. After the introduction of the delivery device, the method contemplates introducing an agent and a gel, such as a bioerodable gel, at the treatment site. Again, the treatment agent and the bioerodable gel may be introduced simultaneously or sequentially as described above.

In yet another embodiment, a kit (e.g., a pre-manufactured package) is disclosed. A suitable kit includes a treatment agent and a compound having a property that forms a bioerodable gel within a mammalian host. The kit may be suitable, in one example, in the methods described above.

In a further embodiment, an apparatus is disclosed. In one embodiment, the apparatus includes a first annular member having a first lumen disposed about a length of the first annular member, and a second annular member coupled to the first annular member having a second lumen disposed about a length of the second annular member, wherein collectively the first annular member and the second annular member have a diameter suitable for placement at a treatment site within a mammalian body. Representatively, distal ends of the first annular member and the second annular member are positioned with respect to one another to allow a combining of treatment agents introduced through each of the first annular member and the second annular member to allow a combining of treatment agents at the treatment site. Such an apparatus is particularly suitable for delivering a multi-component gel material (i.e., individual components through respective annular members) that forms a bioerodable gel within a mammalian host.

BRIEF DESCRIPTION OF THE DRAWINGS

The features, aspects, and advantages of the invention will become more thoroughly apparent from the following detailed description, appended claims, and accompanying drawings in which:

FIG. 5 shows a cross-sectional side view of a distal portion of a second embodiment of a substance delivery apparatus having a co-axial configuration for the delivery of the treatment agent and a compound that forms a gel within a mammalian host.

FIG. 6 shows a cross-sectional front view of a distal end of the delivery apparatus of FIG. 5.

FIG. 7 shows a cross-sectional side view of a distal portion of a second embodiment of a substance delivery apparatus having a co-axial configuration for the delivery of the treatment agent and a compound that forms a gel within a mammalian host.

DETAILED DESCRIPTION

Figure 1:
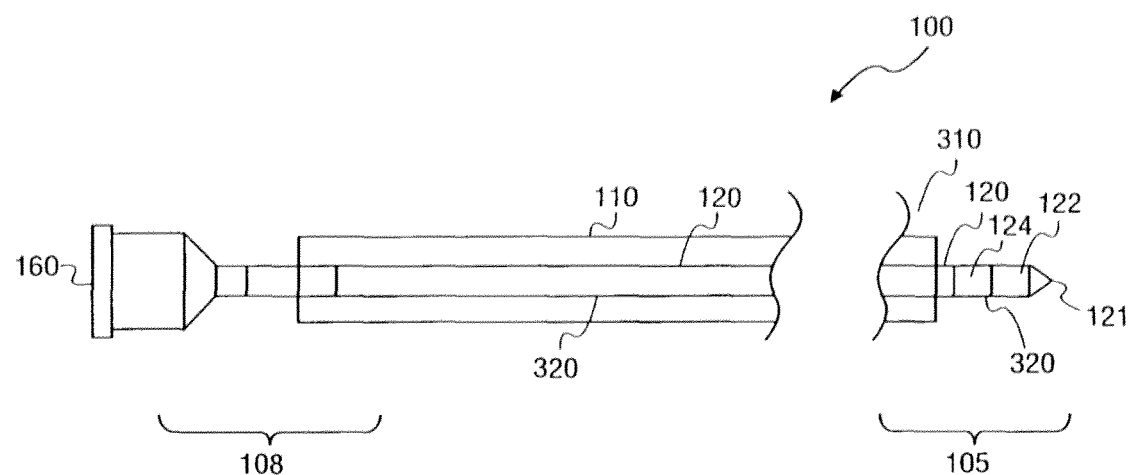
FIG. 1 shows a cross-sectional side view of an embodiment of a substance delivery apparatus including a single delivery device having both a treatment agent and a compound that forms a bioerodable gel in a mammalian host within the delivery apparatus.

In connection with the description of the various embodiments, the following definitions are utilized:

"Therapeutic angiogenesis" refers to the processes of causing or inducing angiogenesis and arteriogenesis.

"Angiogenesis" is the promotion or causation of the formation of new blood vessels in the ischemic region.

"Arteriogenesis" is the enlargement of pre-existing collateral vessels. The collateral vessels allow blood to flow from a well-perfused region of the vessel into the ischemic region.

"Ischemia" is a condition where oxygen demand of the tissue is not met due to localized reduction in blood flow caused by narrowing or occlusion of one or more vessels. Narrowing of arteries such as coronary arteries or their branches, is most often caused by thrombosis or via deposits of fat, connective tissue, calcification of the walls, or restenosis due to abnormal migration and proliferation of smooth muscle cells.

"Occlusion" is the total or partial obstruction of blood flow through a vessel.

"Treatment agent" includes medicaments such as a drug used in the prevention, alleviation, or cure of disease or injury, including, but not limited to, agents directed to specific cellular binding sites (e.g., receptor binding treatment agents) and agents that induce inflammation.

"Specific binding treatment agent" or "receptor binding treatment agent" includes a protein or small molecule that will induce and/or modulate a therapeutic angiogenic response through interaction with a specific binding sites (e.g., a binding within a cell or on a cell surface). Representative treatment agents include, but are not limited to, vascular endothelial growth factor (VEGF) in any of its multiple isoforms, fibroblast growth factors, monocyte chemoattractant protein 1 (MCP-1), transforming growth factor beta (TGF-beta) in any of its multiple isoforms, transforming growth factor alpha (TGF-alpha), lipid factors, hypoxia-inducible factor 1-alpha (HIF-1-alpha), PR39, DEL 1, nicotine, insulin-like growth factors, placental growth factor (PlGF), hepatocyte growth factor (HGF), estrogen, follistatin, proliferin, prostaglandin E1, prostaglandin E2, cytokines, tumor necrosis factor (TNF-alpha), erythropoietin, granulocyte colony-stimulating factor (G-CSF), granulocyte macrophage colony-stimulating factor (GM-CSF), angiogenin, hormones, and genes that encode such substances.

"Non-specific treatment agent" includes various agents that induce inflammation. Examples include bioresorbable inorganic compounds such as sol gel particles and calcium phosphate glass comprising iron; fibrin, gelatin, low molecular weight hyaluronic acid, and chitin; bacterial polysaccharides; and metals.

In the embodiments described herein, a substance delivery device and a method for delivering a substance are disclosed. The delivery device and method described are particularly suitable, but not limited to, local drug delivery in which a treatment agent composition (possibly including multiple treatment agents and/or a sustained-release composition) is introduced via needle delivery to a treatment site within a mammalian host. A kit of a treatment agent composition is also described. One suitable application for a delivery device is that of a catheter device, including a needle delivery system. Suitable therapies include, but are not limited to, delivery of drugs for the treatment of arterial restenosis, therapeutic angiogenesis, or cancer treatment drugs/agents.

Various apparati (devices) and methods described herein can be used as a stand-alone injection needle/catheter during a surgical procedure such as an open heart surgery (e.g., Cabbage Coronary Bypass Graft (CABG)) procedure in which areas of the heart may be treated with, for example, growth factors, for affecting therapeutic angiogenesis, or incorporated into a catheter-based system to access locations that are commonly used in percutaneous translumenal coronary artery (PTCA) procedures. The apparati (devices) and methods may similarly be used in other surgical procedures such as cancer-related procedures (e.g., brain, abdomen, or colon cancer procedures or surgeries). Additionally, various apparati (devices) and methods described herein can be used in conjunction with various catheter-related or endoscopy procedures that generally require minimal invasiveness to deliver a specific drug or growth factor into tissue. Examples of such procedures include, but are not limited to, orthoscopic surgery for joints (e.g., knee), laparoscopic surgery for the abdomen, and thoroscopic procedures related to chest injuries or treatments.

One concern of introducing any treatment agent composition, whether adjacent a blood vessel to affect therapeutic angiogenesis, adjacent a tumor to inhibit tumor growth, or to induce or stimulate collagen growth in orthoscopic procedures, is that the composition remain (at least partially) at the treatment site for a desired treatment duration (or a portion of the treatment duration). In this manner, an accurate dosage may be placed at a treatment site with reduced concern that the treatment agent will disperse, perhaps with serious consequences.

In one embodiment, a composition and technique for retaining a treatment agent at a treatment site (injection site) is described. In one embodiment, a treatment agent and a bioerodable gel are introduced at a treatment site (e.g., an injection site). The bioerodable gel may be introduced prior to, after, or simultaneously with the treatment agent. In one preferred embodiment, the bioerodable gel acts to retain the treatment agent at the treatment site by, representatively, sealing the treatment site or sealing the treatment agent at the treatment site. The use of a bioerodable gel with a treatment agent can reduce the amount of treatment agent backflow from the injection site as well as reduce the load requirement of the treatment agent at the treatment site. For example, a bioerodable gel can decrease the local pressure thereby further resulting in backflow reduction.

In the area of cardiovascular treatment therapies, the treatment agent may be a treatment agent that affects (e.g., induces and/or modulates) therapeutic angiogenesis. Suitable therapeutic angiogenesis treatment agents include, but are not limited to, one or more of a specific binding treatment agent. The treatment agent may further include or be included in a sustained-release matrix that delays the release of the treatment agent over a period of time (such as over several hours to several days). Suitable sustained-release matrix material for therapeutic angiogenesis treatment agents include, but are not limited to, poly(L-lactide), poly(D,L-lactide), poly(glycolide), and poly(lactide-co-glycolide) (PLGA) compositions. Another suitable treatment agent is a non-specific treatment agent such as one that may induce inflammation. Reducing the backflow on introduction of the treatment agent through the use of a gel may inhibit possible thrombogenic effects of a treatment agent that induces inflammation. Although cardiovascular treatment agents are described, it is appreciated that other treatment agents are also contemplated, with one limit being those treatment agents that are compatible with a bioerodable gel material.

In one embodiment, particularly in the case of cardiovascular treatment therapies, the bioerodable gel material is selected to have a property that is non-thrombogenic. Suitable materials include material such as polyphosphoester gels, such as a polyphosphoester with a low glass transition temperature (e.g., POLIHEXOFATE™ polymer, commercially available from Guilford Pharmaceuticals of Baltimore, Md. (a copolymer of 1,4-cyclohexanedimethanol and n-hexylphosphate). Another suitable bioerodable gel is a gel formed from a moderately high glass transition temperature by a resolvable polymer that is plasticized in a pharmaceutical water solvent, such as glucofurol to form the gel. In this latter case, the solvent is selected to be rapidly absorbed by the body leaving the bioerodable material at the injection site. Other polymer materials include poly(glycolic lactic) acid (PLGA), caprolactone, and cyanoacrylate polymers. A third bioerodable gel material is one that is formed by a combination (e.g., mixing, contacting, reacting) of two or more components. One example is an alginate (alginic acid) and calcium chloride that combine to form a gel on contact within a mammalian host.

Accordingly, in one embodiment, a technique is described for introducing a treatment agent at a location in a mammalian host. Specifically, the technique comprises utilizing a delivery device for introducing a treatment agent and a compound that forms a bioerodable gel at a treatment site so as to increase the retention of the treatment agent at the treatment site.

Referring now to the drawings, wherein similar parts are identified by like reference numerals, FIG. 1 illustrates a cross-sectional side view of one embodiment of a delivery device or apparatus. In general, delivery assembly 100 provides an apparatus for delivering a substance, such as a treatment agent or a combination of treatment agents and a composition that forms a bioerodable gel in a mammalian host, to or through a desired area of a blood vessel (a physiological lumen) or tissue in order to treat a localized area of the blood vessel or to treat a localized area of tissue, possibly located adjacent to the blood vessel. Delivery assembly 100 is intended to broadly include any medical device designed for insertion into a blood vessel or physiological lumen to permit introduction (e.g., injection) of a treatment agent.

Referring to FIG. 1, delivery assembly 100, in one embodiment, may be in the form of a catheter delivery device that includes delivery lumen 110 that may be formed in a larger catheter body (not shown). The larger catheter body may include one or more lumens to accommodate, for example, a guidewire, an inflation balloon, and/or an imaging device. Further, such a catheter body may accommodate one or more delivery lumens, such as delivery lumen 110. Delivery lumen 110, in this example, extends between distal portion 105 and proximal portion 108 of delivery assembly 100. Delivery lumen 110 can be made from any suitable material, such as polymers and co-polymers of polyamides, polyolefins, polyurethanes, and the like.

In one embodiment, delivery assembly 100 includes needle 120 movably disposed within delivery lumen 110. Needle 120 is, for example, a stainless steel hypotube that extends a length of the delivery assembly. Needle 120 includes a lumen with an inside diameter of, representatively, 0.16 inches (0.40 centimeters). In one example for a retractable needle catheter, needle 120 has a length on the order of 40 inches (1.6 meters) from distal portion 105 to proximal portion 108. At an end of proximal portion 108 is adapter 160 of, for example, a female luer housing.

Referring to distal portion 105 of delivery assembly 100, there is shown needle 120 having treatment agent 122 disposed at or near its tip (tip 121). In one example, treatment agent 122 is a material selected for its ability to affect therapeutic angiogenesis.

Disposed proximally (as viewed) to treatment agent 122 in needle 120 is gel material 124 that has a property such that it will form a bioerodable gel when placed at a treatment site (e.g., in the wall of a blood vessel, in a periadventitial space, in an area radially outward from a periadventitial space, etc.). Suitable materials for gel material include, but are not limited to, the polyphosphoester gels and bioresorbable polymers (possibly dissolved in a solvent), such as PLGA, caprolactone or cyanoacrylate polymers referenced above.

One technique to load treatment agent 122 and gel material 124 into a catheter delivery device is by creating an area (volume) of reduced pressure in needle 120 by, for example, a syringe bore. First, distal portion 105 is placed in a solution having a selected concentration of gel material 124, such as on the order of about 11 microliters (approximately 3-4 milligrams of polymer or 25 weight percent). Through a pressure differential, a desired amount of gel material 124 is taken up by needle 120.

Following the loading of gel material 124, needle 120 (distal portion 105 of needle 120) is placed in a solution comprising a selected concentration of treatment agent 122 which, as is appreciated, will vary with the particular treatment and/or treatment agent. Again by a reduced pressure in needle 120, a desired amount of a treatment agent is taken up by needle 120.

In certain instances, it may be desired to combine the treatment agent and the gel material into a single composition and introduce the single composition to a treatment site. Such an instance may be one where the combination (e.g., mixing) of the gel material and the treatment agent does not inhibit (or minimally inhibits) the properties of the treatment agent. One example in the context of cardiovascular treatment therapies is a treatment agent that affects therapeutic angiogenesis by inducing inflammation, such as a metal (e.g., Au). It is appreciated in such instances that a solution composition of a gel material and a treatment agent may be loaded into needle 120 by a pressure differential as described or may be introduced through adaptor 160 (such as through a needle luer).

Once loaded, such as described above, treatment agent 122 and gel material 124 may be introduced according to known substance delivery techniques such as by advancing tip 121 of needle 120 into tissue (e.g., a wall of a blood vessel) and delivering the treatment agent and gel material through back pressure (e.g., pressure applied at proximal portion 108, such as by a needle luer). Needle 120 may form a wound (wound opening) in tissue at the treatment site. The introduction of gel material 124 following treatment agent 122 will tend to contain (retain) treatment agent 122 within the wound opening, thus reducing backflow.

Figure 2:
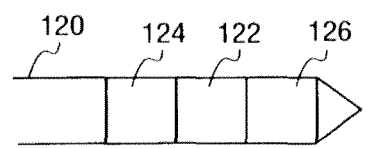
FIG. 2 shows a cross-sectional side view of a second embodiment of a delivery apparatus having both a treatment agent and a compound that may form a bioerodable gel in a mammalian host.

FIG. 2 shows an alternative loading arrangement within needle 120. In this embodiment, treatment agent 122 is disposed between gel material. Again, each of the materials may be loaded in needle 120 through pressure differential techniques. One order is loading gel material 124, followed by treatment agent 122, followed by gel material 126.

The configuration shown in FIG. 2 of treatment agent 122 disposed between gel material 124 and gel material 126 may be used, representatively, in a situation where it is desired to retain the treatment agent within needle 120 until delivery (e.g., to prevent the loss of a portion of treatment agent 122 prior to delivery at a treatment site within a mammalian host).

Figure 3:
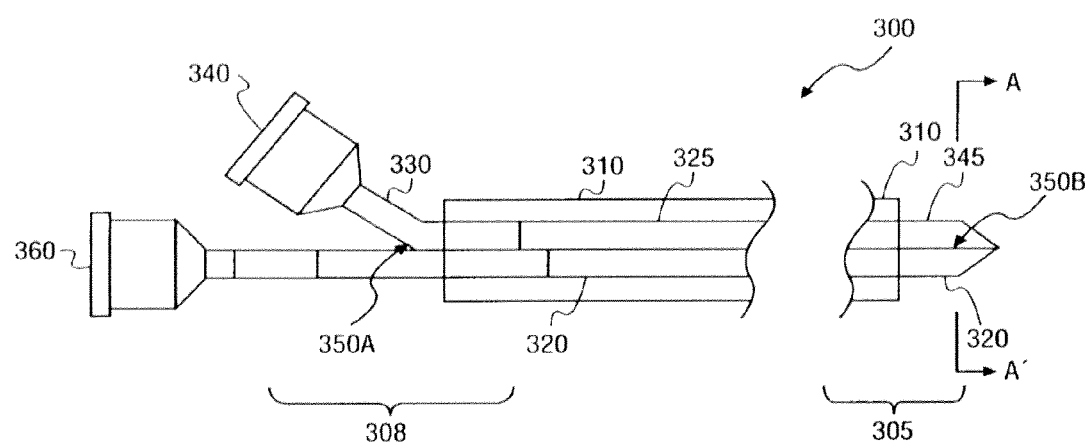
FIG. 3 illustrates a simplified, cross-sectional side view of an embodiment of a substance delivery apparatus in the form of a catheter assembly including linear-aligned delivery lumens for a treatment agent and a compound that forms a bioerodable gel within a mammalian host.

FIG. 1 and FIG. 2 describe embodiments of techniques for introducing a treatment agent and a gel material, such as a bioerodable gel material, to a treatment site within a mammalian host (e.g., human). Such embodiments are particularly suitable for use with gel material that may be introduced in a single composition either as a gel (e.g., dispersed in solvent) or to form a gel within a mammalian host. FIG. 3 presents an embodiment of an apparatus that may be used to introduce a material that is a combination of two materials that, when combined in a mammalian host, form a bioerodable gel. One example of such a gel material is an alginate and calcium chloride.

FIG. 3 presents delivery assembly 300 of, for example, a catheter-compatible device or apparatus. Delivery assembly 300 includes delivery lumen 310 of, for example, a polymer material that may be formed in a larger catheter body (not shown). The larger catheter body may include one or more other lumens to accommodate, for example, an additional delivery device lumen, a guidewire an inflation balloon, and/or imaging device. Delivery lumen 310, in this example, extends between distal portion 305 and proximal end 308 of delivery assembly 300.

Figure 4:
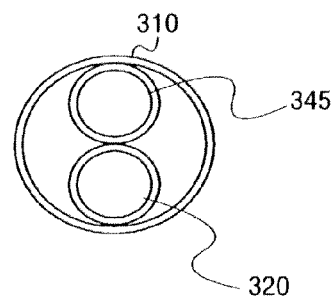
FIG. 4 shows a cross-sectional front view of a distal end of the delivery apparatus of FIG. 3.

In one embodiment, delivery assembly 300 includes main needle 320 disposed within delivery lumen 330. Main needle 320 is movably disposed within delivery lumen 330. Main needle 320 is, for example, a stainless steel hypotube that extends a length of the delivery assembly. Main needle 320 includes a lumen with an inside diameter of, for example, 0.08 inches (0.20 centimeters). In one example for a retractable needle catheter, main needle 320 has a needle length on the order of 40 inches (1.6 meters) from distal portion 305 to proximal portion 308. Delivery lumen 310 also includes separate, possibly smaller diameter, auxiliary lumen 325 extending, in this example, co-linearly along the length of the catheter (from a distal portion 305 to proximal portion 308). Auxiliary lumen 325 is, for example, a polymer tubing of a suitable material (e.g., polyamides, polyolefins, polyurethanes, etc.). At distal portion 305, auxiliary lumen 325 is terminated to auxiliary needle end 345 co-linearly aligned with a delivery end of needle 320. Auxiliary lumen 325 may be terminated to auxiliary needle end 345 with a radiation-curable adhesive, such as an ultraviolet curable adhesive. Auxiliary needle end 345 is, for example, a stainless steel hypotube that is joined co-linearly to the end of main needle 320 by, for example, solder (illustrated as joint 350B). Auxiliary needle end 345 has a length on the order of about 0.08 inches (0.20 centimeters). FIG. 4 shows a cross-sectional front view through line A-A' of delivery assembly 300. FIG. 4 shows main needle 320 and auxiliary needle 345 in a co-linear alignment.

Referring to FIG. 3, at proximal portion 308, auxiliary lumen 325 is terminated to auxiliary side arm 330. Auxiliary side arm 330 includes a portion extending co-linearly with main needle 320. Auxiliary side arm 330 is, for example, a stainless steel hypotube material that may be soldered to main needle 320 (illustrated as joint 350A). Auxiliary side arm 330 has a co-linear length on the order of about, in one example, 1.2 inches (3 centimeters).

The proximal end of main needle 320 includes adaptor 360 for accommodating a substance delivery device (e.g., a substance of a treatment agent or bioerodable gel material). Adaptor 360 is, for example, a molded female luer housing. Similarly, a proximal end of auxiliary side arm 330 includes adaptor 340 to accommodate a substance delivery device (e.g., a female luer housing).

The design configuration described above with respect to FIG. 3 is suitable for introducing a bioerodable gel into two parts form. For example, a gel formed by a combination (mixing, contact, etc.) of an alginate and calcium chloride. Representatively, a 3.5 percent of an alginate solution may be introduced by a one cubic centimeters syringe at adaptor 360 through main needle 320. At the same time or shortly before or after, a solution of calcium chloride may be introduced with a one cubic centimeter syringe at adaptor 340. When the alginate and calcium chloride combine at the exit of delivery assembly 300 (at a treatment site), the materials combine (mix, contact) to form a bioerodable gel. One example of a suitable amount of two material gel components for use in a cardiovascular treatment therapy is approximately 200 microliters of alginate solution and one milliliter calcium chloride. Excess calcium chloride may flush through the host as a saline solution. In one embodiment, a desired amount of a treatment agent may be introduced with the alginate solution.

FIG. 5 shows a second embodiment of a delivery assembly for delivering a two part composition to a treatment site through a needle. In one embodiment, the two part composition may be components that collectively form a bioerodable gel once inside a mammalian host.

FIG. 5 illustrates a co-axial alignment for delivering a two part composition to a treatment site. In this example, delivery assembly 400 includes delivery lumen 410 to accommodate any co-axial needle configuration. Delivery lumen 410 extends, for example, the length of the catheter assembly, from a distal portion to a proximal portion. In the embodiment illustrated in FIG. 5, only the distal portion of delivery assembly 400 is illustrated. The proximal portion may be similar to that described above with respect to FIG. 3 (e.g., separate ports for introducing separate compositions into a single delivery lumen).

Referring to FIG. 5, delivery assembly 400 includes main needle portion 420 of, for example, a stainless steel hypotube material having a lumen diameter on the order of 0.08 inches (0.20 centimeters) and extending the length of the delivery assembly (from distal portion to proximal portion). Surrounding main needle portion 420, in this example, is auxiliary needle portion 445. Auxiliary needle portion 445 has a larger diameter than the diameter of main needle portion 220 such that an opening or a lumen is created between main needle portion 420 and auxiliary portion 445 to allow the introduction of a material therethrough. An exemplary interior diameter of auxiliary needle portion 445 is on the order of 0.16 inches (0.40 centimeters).

Auxiliary needle portion 445 is, for example, stainless steel hypotube material that may be coupled to main needle portion 420 through support vanes 455 (e.g., by laser welding support vanes to auxiliary needle portion 445 and main needle portion 420). Auxiliary needle portion 445 may extends the entire length of needle assembly 400 (i.e., from distal portion to proximal portion) or may comprise only a tip or end portion of, for example, 0.02 to 0.08 inches (0.05 to 0.2 centimeters). In the latter case, auxiliary lumen 425 of, for example, a polymer material may extend through delivery assembly 400 and be terminated to auxiliary needle portion 445 with, for example, a radiation-curable adhesive.

FIG. 5 shows main needle portion 420 having an end (a distal end) portion extending beyond auxiliary needle portion 445. In this manner, the distal end of delivery assembly 420 may be configured as an angle tip, with an angle α, of between, for example, 15 degrees to 45 degrees to allow the penetration of tissue with the end of delivery device 400. The angle α extends around the assembly.

FIG. 6 shows a cross-sectional front view of delivery assembly 400 through line B-B' of FIG. 5. FIG. 6 shows main needle portion 420 co-axially surrounded by auxiliary needle portion 445 with support vanes 455 extending between main needle portion 420 and auxiliary needle portion 445.

In an embodiment where a two part composition of an alginate and calcium chloride is introduced to form a bioerodable gel, the low viscosity medium (calcium chloride) may be introduced (injected) through the outer annular portion (defined by the lumen between main needle portion 420 and auxiliary needle portion 445). The higher viscosity medium calcium chloride may be introduced through the lumen defined by main needle portion 420.

FIG. 7 shows a cross-sectional side view of a third embodiment of a delivery device for delivering a multi-component material to a treatment site. The configuration shown in FIG. 7 is also a co-axial arrangement (similar to FIGS. 5 and 6). Delivery assembly 500 includes delivery lumen 510, main needle portion 520, auxiliary portion 545, co-axially surrounding main needle portion 520. In this embodiment, main needle portion 520 extends, representatively, the length of delivery assembly 500 (from distal portion to proximal portion). Auxiliary needle portion 545 is a tip portion of, for example, a stainless steel hypotube material that may be coupled to main needle portion 520 by support vanes 555. Auxiliary lumen 525 of, for example, a polymer material may extend the length of delivery assembly 500 and be terminated at auxiliary needle portion 545 with an adhesive (e.g., a radiation-curable adhesive).

In the embodiment shown in FIG. 7, the distal end of delivery assembly 500 includes an angle tip formed by main needle portion 520 and auxiliary needle portion 545. From this example, the tip is a single angle tip, with an end angle, α, on the order of 15 degrees to 45 degrees. In this manner, the angle tip allows for insertion into tissue.

Figure 8:
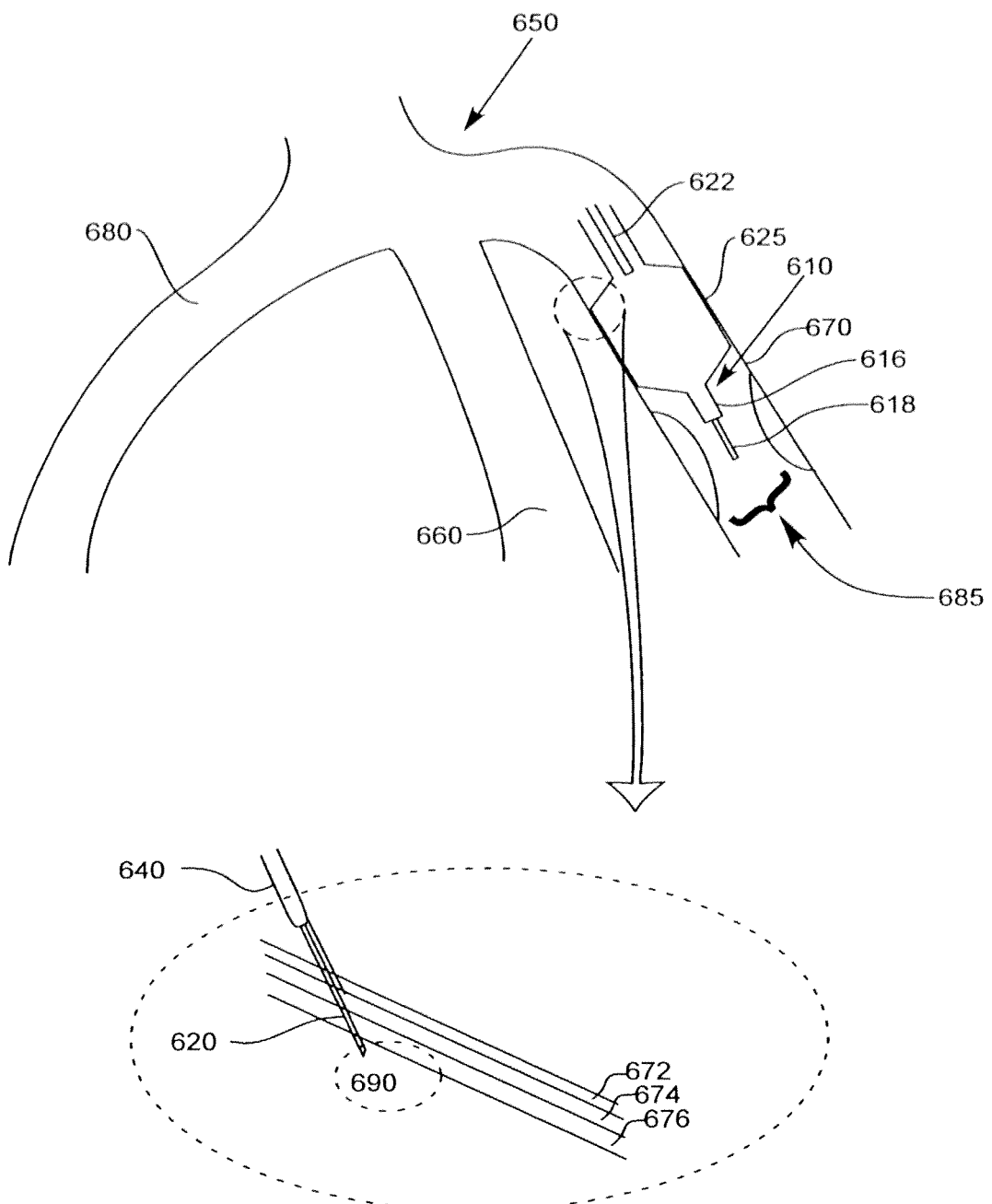
FIG. 8 schematically illustrates a coronary artery network with a catheter assembly introduced therein.

The catheter assemblies described with reference to FIGS. 1-7 may be used to introduce a treatment agent and a gel such as described above at a desired location. FIG. 8 illustrates one technique.

FIG. 8 illustrates components of a coronary artery network. In this simplified example, vascular 650 includes left anterior descending artery (LAD) 660, left circumflex artery (LCX) 670 and right coronary artery (RCA) 680. Occlusion 685 is shown in LCX 670. Occlusion 685 may limit the amount of oxygenated blood flow through LCX 670 resulting in ischemia in the tissues distal (downstream) to the occlusion. To improve the function of the artery network, it is generally desired to either remove occlusion 685 (for example, through an angioplasty procedure), bypass occlusion 685 or induce therapeutic angiogenesis to make-up for the constriction in the ischemic region.

With reference to FIG. 8, in a one procedure, guidewire 618 is introduced into, for example, the arterial system of the patient (e.g., through the femoral artery) until the distal end of guidewire 618 is upstream of a narrowed lumen of the blood vessel (e.g., upstream of occlusion 685). Delivery assembly 600 (in this example, a balloon catheter device) is mounted on the proximal end of guidewire 618 and advanced over guidewire 618 via lumen 616 until positioned as desired. In the example shown in FIG. 8, delivery assembly 600 is positioned so that catheter balloon 625 and a delivery lumen 640 (see, e.g., delivery lumen 110 (FIG. 1); delivery lumen 310 (FIG. 3); delivery lumen 410 (FIG. 5); delivery lumen 510 (FIG. 7)) are upstream of the narrowed lumen of LCX 670. Angiographic or fluoroscopic techniques may be used to place delivery assembly 600. Once catheter balloon 625 is placed, a treatment site of the blood vessel may be identified by further imaging techniques, including but not limited to, optical coherence tomography, ultrasonic, or magnetic resonance techniques. An example of an optical imaging technique is described in co-pending commonly-assigned U.S. patent application Ser. No. 10/011,071 where catheter balloon 630 is subject to low inflation pressure and guidewire 618 is removed and replaced in one embodiment with an optical fiber. In the catheter assembly shown in FIG. 8, the imaging portion of an imaging device (e.g., OCT, ultrasonic, etc.) may be within the imaging lumen as the catheter is positioned. Once positioned, in this case upstream of occlusion 685, the imaging assembly is utilized to view the blood vessel and identify the various layers of the blood vessel.

The imaging assembly may provide viewable information about the thickness or boundary of the intimal layer 672, media layer 674, and adventitial layer 676 of LCX 670. LCX 670 is viewed and the layer boundary is identified or a thickness of a portion of the blood vessel wall is imaged (and possibly measured). The treatment site may be identified based on the imaging (and possibly measuring). In one example, the treatment site is a peri-adventitial site (e.g., site 678) adjacent to LCX 670.

After identifying a treatment site, catheter balloon 625 is dilated as shown in FIG. 8 by, for example, delivering a liquid or gas to catheter balloon 625 through inflation lumen 622. Delivery lumen 640, in this example, is coupled to a proximate tapered wall of catheter balloon 620 such that, as catheter balloon 620 is inflated, delivery lumen 640 moves proximate to or contacts the blood vessel wall adjacent to the treatment site. The delivery assembly (device) described is similar in certain respects to the assembly (device) described in commonly-owned U.S. patent application Ser. No. 09/746, 498 (filed Dec. 21, 2000) titled "Directional Needle Injection Drug Delivery Device," of Chow, et al., that is incorporated herein by reference. Needle 630 is then advanced a distance into the wall of the blood vessel. A real time image may be used to advance needle 620. Alternatively, the advancement may be based on a measurement of the blood vessel wall or layer boundary derived from an optical image. Needle 620 may be, for example, similar to designs described above with reference to FIGS. 1 and 2 (needle 120). Alternatively, needle 620 may be a dual needle assembly similar to delivery assembly 300 described with reference to FIGS. 3 and 4 (e.g., main needle 320 and auxiliary lumen 325/auxiliary needle 345). As a further alternative, needle 620 may be similar to the embodiment described with reference to FIGS. 5 and 6 (main needle portion 420 and auxiliary needle portion 445) or FIG. 7 (main needle portion 520 and auxiliary needle portion 545).

In the embodiment shown in FIG. 8, needle 620 is advanced through the wall of LCX 670 to peri-adventitial site 690. Once in position, a treatment agent and gel are introduced through needle 620 to the treatment site (e.g., peri-adventitial site 690).

In the preceding detailed description, specific embodiments are presented. Those embodiments include apparati (devices) and methods for introducing a treatment agent and a gel at a treatment site within a mammalian body. Cardiovascular treatment therapies in particular are highlighted. It will, however, be evident that various modifications and changes may be made thereto without departing from the broader spirit and scope of the claims. For example, contemplated treatment therapies include therapies, in addition to cardiovascular treatment therapies, where blood vessels or tissues are identified for localized treatment agents in the context of surgery or other medical procedure. The specification and drawings are, accordingly, to be regarded in an illustrative rather than a restrictive sense.

What is claimed is:

1. A method comprising:
    introducing a delivery device into a blood vessel of a mammalian host, the delivery device having a first delivery port and a second separate delivery port, the first delivery port and the second delivery port arranged in one of a co-linear and a co-axial arrangement; and
    introducing a bioerodable gel material and a treatment agent wherein the gel material is a product of a combination of a first component and a second component and one of the first component and the second component comprises the treatment agent and the first component is introduced to a treatment site through the first delivery port, and the second component is introduced to the treatment site through the second delivery port,
    wherein the treatment site comprises a location, with reference to a lumen of the blood vessel, beyond a medial layer of the blood vessel.

2. The method of claim 1, wherein the treatment site is associated with a blood vessel.

3. The method of claim 2, wherein introducing the treatment agent comprises:
    advancing the delivery device a distance into a wall of the blood vessel to the treatment site; and
    after advancing the delivery device, introducing the treatment agent through the delivery device.

4. The method of claim 3, wherein the treatment site comprises a periadventitial site.

5. The method of claim 1, wherein the treatment site is selected from the group consisting of a thoroscopic surgery site, an orthoscopic surgery site, and a laparoscopic surgery site.

6. A method comprising:
    positioning a delivery device at a location in a blood vessel;
    advancing the delivery device a distance into a wall of the blood vessel to a treatment site beyond a medial layer of the blood vessel; and
    after advancing the delivery device, introducing a treatment agent and a gel material at the treatment site.

7. The method of claim 6, wherein the treatment agent and the gel material are introduced as a combination.

8. The method of claim 7, wherein the gel material is a product of a combination of a first component and a second component and one of the first component and the second component comprises the treatment agent.

9. The method of claim 8, wherein introducing the gel material comprises:
    introducing a delivery device having a first delivery port and a second separate delivery port, the first delivery port and the second delivery port arranged in one of a co-linear and a co-axial arrangement; and
    introducing the first component to the treatment site through the first delivery port; and
    introducing the second component to the treatment site through the second delivery port.

10. The method of claim 6, wherein the treatment site comprises a periadventitial site.

11. The method of claim 6, wherein introducing the gel material follows the introduction of the treatment agent.

12. The method of claim 6, wherein introducing the gel material precedes the introduction of the treatment agent.

* * * * *